United States Patent [19]
Verman et al.

[11] Patent Number: 6,069,934
[45] Date of Patent: May 30, 2000

[54] X-RAY DIFFRACTOMETER WITH ADJUSTABLE IMAGE DISTANCE

[75] Inventors: Boris Verman, Troy; Licai Jiang, Rochester Hills, both of Mich.

[73] Assignee: Osmic, Inc., Troy, Mich.

[21] Appl. No.: 09/056,654

[22] Filed: Apr. 7, 1998

[51] Int. Cl.⁷ .................................................. G01N 23/207
[52] U.S. Cl. ............................................... 378/73; 378/81
[58] Field of Search .................... 378/79, 81, 73

[56] References Cited

U.S. PATENT DOCUMENTS

| | | |
|---|---|---|
| 3,636,347 | 1/1972 | Poot . |
| 4,364,122 | 12/1982 | Wolfel et al. ............................. 378/73 |
| 4,525,853 | 7/1985 | Keem et al. .............................. 378/89 |
| 4,958,363 | 9/1990 | Nelson et al. ............................ 378/85 |
| 5,027,377 | 6/1991 | Thoe ....................................... 378/145 |
| 5,127,039 | 6/1992 | Hesch ...................................... 378/79 |
| 5,353,324 | 10/1994 | Kitano ..................................... 378/73 |
| 5,359,640 | 10/1994 | Fink et al. ............................... 378/79 |
| 5,373,544 | 12/1994 | Goebel .................................... 378/71 |
| 5,418,828 | 5/1995 | Carpenter ................................. 378/71 |
| 5,459,770 | 10/1995 | Salje ...................................... 378/71 |
| 5,604,782 | 2/1997 | Cash ....................................... 378/85 |

*Primary Examiner*—David P. Porta
*Assistant Examiner*—Drew A. Dunn
*Attorney, Agent, or Firm*—Harness, Dickey & Pierce, P.L.C.

[57] ABSTRACT

An x-ray diffractometer system comprising an x-ray optic which directs x-rays, a sample placed into said directed x-rays, wherein said sample diffracts said directed x-rays, creating a diffraction pattern, a translation stage coupled to said sample for moving said sample within said directed x-rays, whereby the resolution, angular range, and intensity of said diffraction pattern may be adjusted, and an x-ray detector for registering said diffraction pattern.

32 Claims, 4 Drawing Sheets

X-RAY DIFFRACTOMETER WITH ADJUSTABLE IMAGE DISTANCE

BACKGROUND OF THE INVENTION

The present invention relates to an x-ray diffractometer, spectrometer, or other x-ray analysis application. More specifically the present invention relates to an improved method of generating and measuring the diffraction, spectrometry, or other x-ray pattern for a sample.

A common method used to study crystal structures is x-ray diffraction. The method is based on illuminating a sample crystal with a beam of x-rays. A portion of the x-ray beam is not able to travel directly through the sample crystal, rather some rays are deflected or diffracted and emerge from the sample at varying angles. The incident x-rays make their way along the spaces between the atoms of the crystal or are deflected by the atoms. A sensor is used which detects the x-ray diffraction pattern generated by the x-rays as they emerge from the sample crystal. This diffraction pattern corresponds to the atomic structural arrangement of the crystal. Such a system is known in the art as an x-ray diffractometer.

Traditionally one changes the resolution and the angular range of a diffractometer by adjusting the distance between the sample and the detector. The detector has always been the moving part in previous designs with the sample mounted in a fixed position with respect to the x-ray source. A collimated beam is often used so that the beam spot on the detector will not change significantly while the sample-detector distance is changed. This collimated beam for certain applications does not contain enough flux to generate a readable diffraction pattern.

A focused x-ray beam can be used to obtain higher flux densities upon the sample than is possible with a collimated beam. When generating a diffraction pattern of a sample, the focused x-ray beam is normally directed through the sample and focused on to the detector to obtain the best resolution. The focusing optics traditionally used are bent total reflection mirrors. When the sample-detector distance is changed, the focal length of the mirrors is readjusted to place the focal point on the detector by bending the mirrors. The size and intensity of the focal spot can be adjusted by bending the mirrors. This bending process is a time consuming and relatively inefficient task.

The reflective surfaces in the present invention are configured as multilayer or graded-d multilayer Bragg x-ray reflective surfaces. Bragg structures only reflect x-ray radiation when Bragg's equation is satisfied:

$$n\lambda = 2d \sin(\theta)$$

where

| | | |
|---|---|---|
| n | = | the order of reflection |
| $\lambda$ | = | wavelength of the incident radiation |
| d | = | layer-set spacing of a Bragg structure or the lattice spacing of a crystal |
| $\theta$ | = | angle of incidence |

Multilayer or graded-d multilayer Bragg mirrors are optics with a fixed focal point which utilize their inherent Bragg structure to reflect narrow band or monochromatic x-ray radiation. The bandwidth of the reflected x-ray radiation can be customized by manipulating the optical and multilayer parameters. The d-spacing of the multilayer mirror can be tailored through lateral grading in such a way that the Bragg condition is satisfied at every point on the multilayer mirror. The d-spacing may also be changed depthwise to control the bandpass of the multilayer mirror. The d-spacing depth may vary as a function of depth or the d-spacing may be held constant for each layer.

Multilayer mirrors have the ability to increase the flux by more than one order of magnitude with a fine focus x-ray tube, as compared with total reflection mirrors. Multilayer mirrors, because of their monochromatic output, could also reduce any unwanted spectrum. For example, in certain applications the K$\beta$ radiation emitted from a source and transmitted through a sample could be reduced by thousands of times. With fixed focal point multilayer optics, the traditional resolution adjustment scheme is not suitable because any bending of a multilayer optic will impair the reflective aspects of their Bragg structure. The present invention includes a new technique, which takes advantage of the large amount of narrow bandpass or monochromatic flux generated by multilayer or graded-d multilayer mirrors and maintains the flexibility of changing the resolution and angular range of a diffraction pattern.

The procedure utilized in the present invention involves moving the sample coaxially and rotationally relative to x-ray beam reflective optics during x-ray diffraction analysis. The x-ray reflective optics are static while the sample is maneuvered through varying intensities of the focused x-ray beam, eliminating the need for optics with variable focal lengths. The movement of the sample through the focused x-ray beam will change the resolution, angular range, and intensity of the sample diffraction pattern. This method will allow a more efficient use of multilayer or graded-d multilayer mirrors as opposed to current technology such as total reflection mirror technology. The focal length of the multilayer optics used will be a constant, removing the time consuming task of adjusting focal lengths for total reflection mirrors.

The movement of the sample does not prohibit the movement of the detector. The detector may also be moved in certain applications with or without movement of the sample. In small sample applications where a sample is placed directly upon the focal point of a focusing optic, movement of the detector may be desired.

SUMMARY OF THE INVENTION

The present invention is a method and apparatus for generating and examining the x-ray diffraction or other x-ray pattern of a sample by moving a sample relative to an x-ray beam and an x-ray detector. An object of the present invention is to allow adjustments in the resolution, flux intensity, and angular range of a diffractometer utilizing any known type of x-ray optic or x-ray reflector. Another object of the present invention is to increase x-ray flux incident on a sample through the use of multilayer or graded-d multilayer Bragg structures while still maintaining the flexibility of the system.

DETAILED DESCRIPTION OF THE PREFERRED EMBODIMENT

Figure 1:
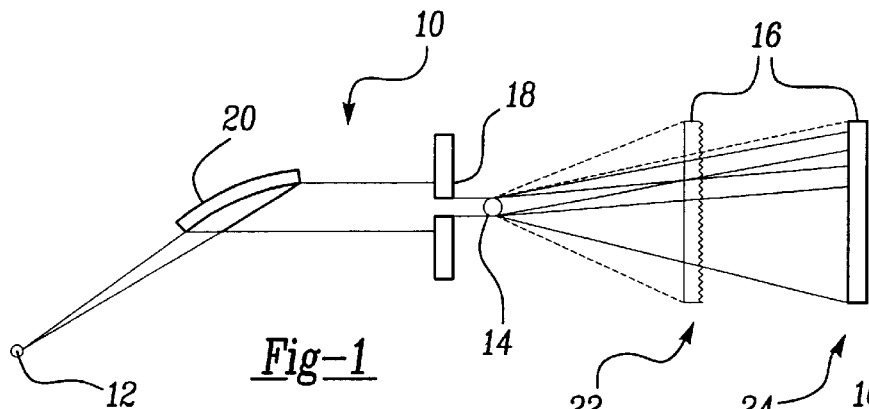
FIG. 1 is a diagrammatic view of a traditional x-ray diffractometer.

FIG. 1 is a diagrammatic view of a traditional x-ray diffractometer 10. An x-ray source 12 is directed towards a parabolic total reflection mirror 20 or other optic which collimates the x-ray beam and directs it through a slit 18. The slit 18 eliminates the x-rays that will not contact sample 14. Sample 14 then diffracts the x-ray beam and detector 16 registers the diffraction pattern.

In this traditional diffractometer 10, the resolution and angular range are adjusted by changing the distance between the sample 14 and the detector 16. The detector 16 in this type of diffractometer is always the moving part of the design. As shown in FIG. 1, the detector 16 can be moved to two positions 22 and 24. At position the angular range is higher than at position 24 but the resolution is lower. Position 24 has a higher resolution but the angular range of the diffraction pattern is lower.

Figure 2:
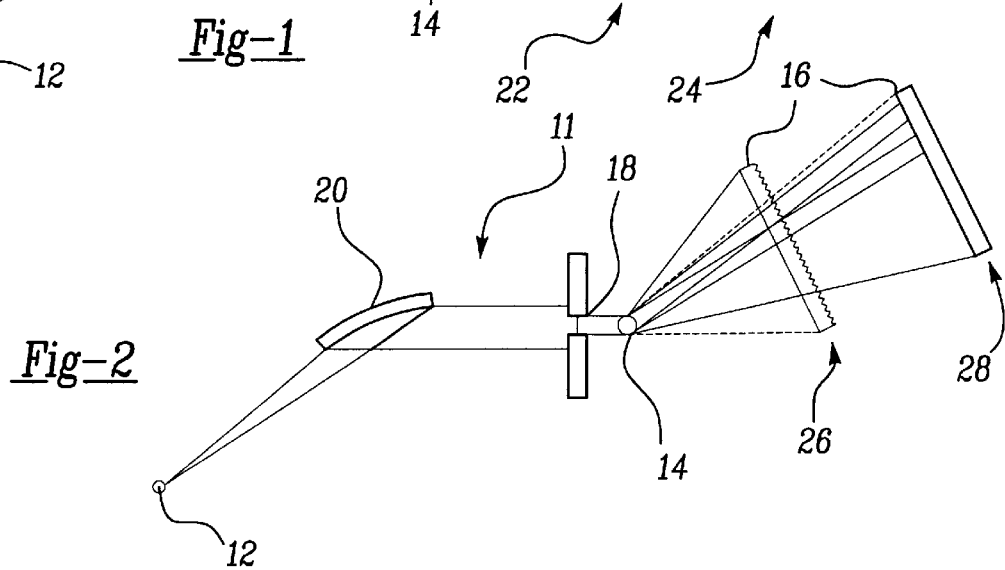
FIG. 2 is another diagrammatic view of traditional x-ray diffractometer.

FIG. 2 is another diagrammatic view of a traditional x-ray diffractometer 11. This view is similar to FIG. 1 but the detector 16 is shown at positions 26 and 28. In order to increase the angular range of the detection system, detector 16 can be moved with two independent adjustments. The detector 16 can be moved in linear fashion, increasing or decreasing its distance from the sample 14, and rotated about the sample 14. Position 26 shows the detector 16 rotated about sample 14. Position 28 shows the detector 16 at this same angular position but further from the sample 14. The resolution and angular range follow the same model as in FIG. 1. The angular range is greater at position 26 than position 28, but position 28 has greater resolution.

Figure 3A:
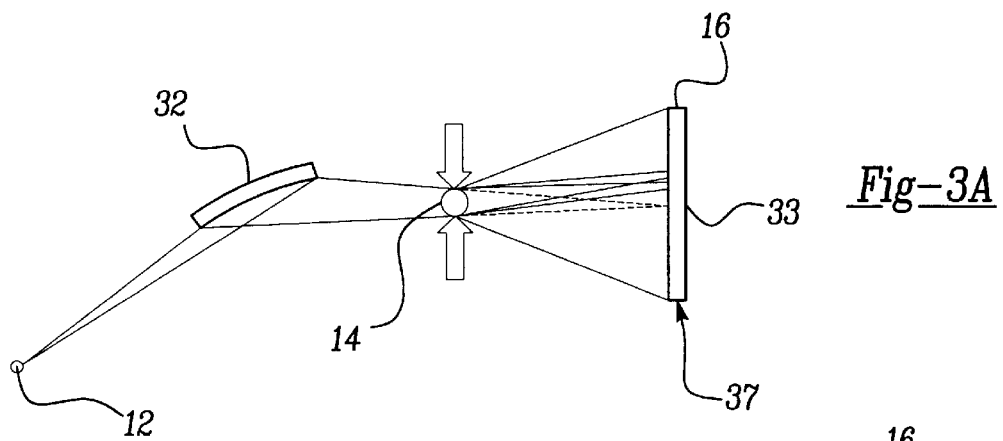
FIGS. 3a and 3b are diagrammatic views of a traditional x-ray diffractometer using a focused beam layout.
Figure 3B:
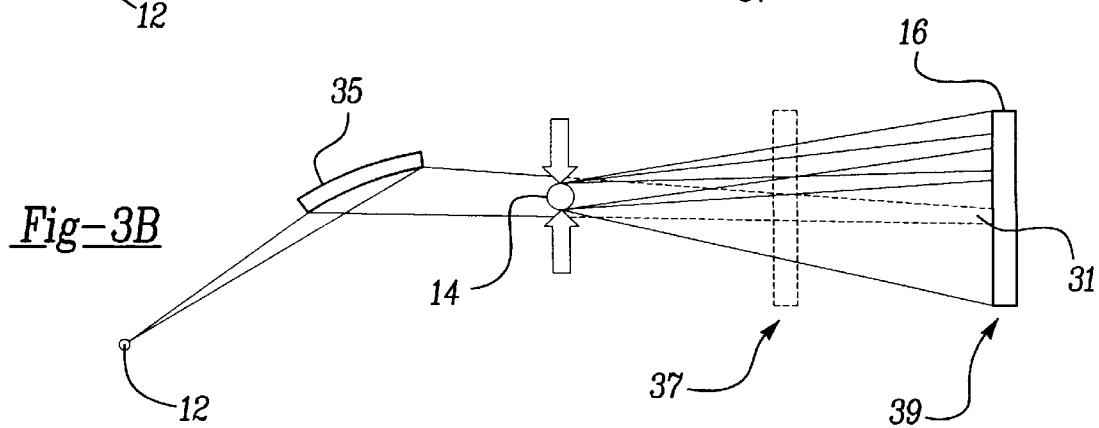

FIGS. 3a and 3b are diagrammatic views of a traditional x-ray diffractometer using a focused beam layout. An x-ray source 12 is directed towards a total reflection elliptical mirror 32 which focuses the x-ray beam through sample 14 at focal point 33 on detector 16 located at position 37. This focusing increases the amount of x-ray flux concentrated upon the sample 14 and the intensity of the diffraction pattern upon detector 16. When the focal point 33 of the elliptical mirror 32 is changed the flux on the sample 14 is also changed.

The focal point 33 of the system is changed by the bending of the mirror 32. As shown in FIG. 3b the detector 16 has been moved to position 39 and the focal point 31 has been adjusted to the same position. This bending of the mirror 32 to change the flux upon the sample 14 and the angular range of the diffraction pattern, is a relatively inefficient time consuming process.

Figure 4A:
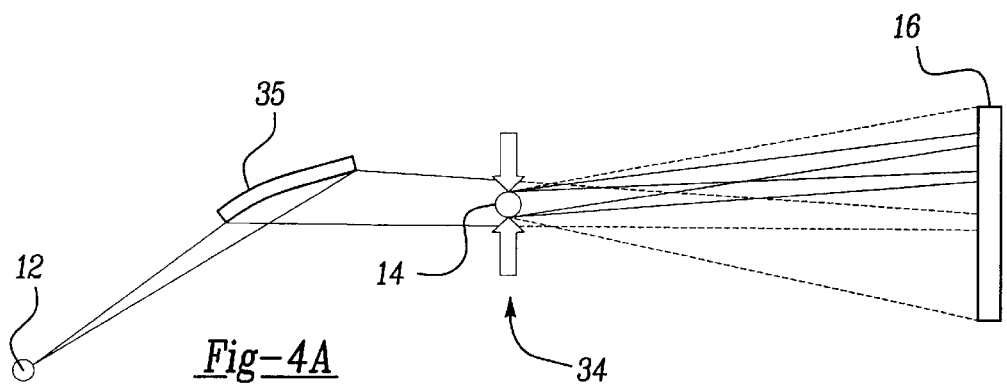
FIGS. 4a and 4b are diagrammatic views of one embodiment of the present invention illustrating its method of operation.
Figure 4B:
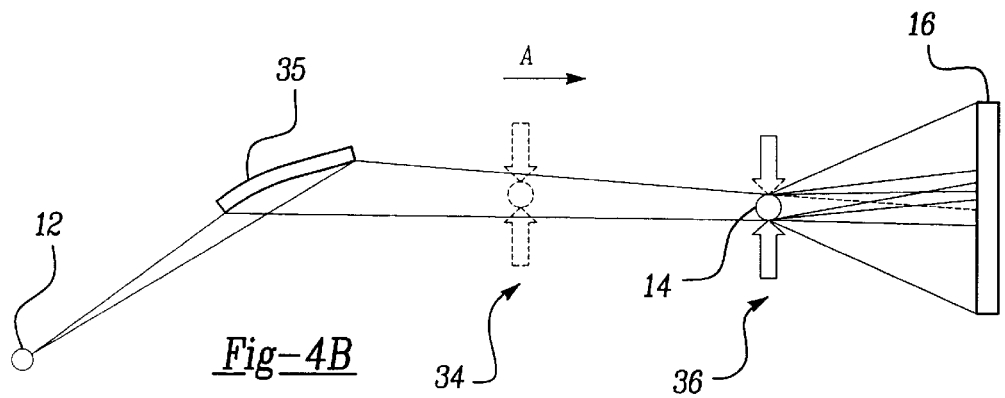

FIGS. 4a and 4b show a first embodiment of the present invention illustrating its operation. In this first embodiment, x-ray reflector 35 is an elliptically shaped focusing multilayer Bragg reflector but is not limited to such. The x-ray reflector 35 can assume a parabolic shape, a spherical shape, or any other shape which is found beneficial in directing x-rays. The multilayer Bragg configuration of the reflector 35 can deliver more flux than total reflection mirrors, especially with fine focusing x-rays sources. The reflected x-ray flux can be narrow band or monochromatic and could reach intensities tens of times greater than that of a total reflection mirror and eliminate unwanted spectrum such as Kβ in the diffraction pattern. Since both curvature and d-spacing must be permanently configured to satisfy Bragg's law, the curvature and therefore the focal length of the reflector 35 cannot be changed. The resolution of the diffraction pattern in this embodiment is changed by moving the sample 14 within the focused x-ray beam rather than just moving the detector 16, although the detector 16 may be moved in conjunction with the sample 14 to further improve the diffraction pattern. The sample 14 is placed in a holding means which can contain a goniometer to rotate the sample 14 in at least one direction. A translation stage moves the sample 14 coaxially with reference to the x-ray beam.

As can be seen in FIGS. 4a and 4b, when the sample 14 is located at position 34 the diffraction pattern has higher resolution, lower flux and smaller angular range than at position 36. When the sample 14 is moved closer to the detector 16 at position 36, more flux can be used for diffraction but the resolution on the detector 16 is decreased. This result is generated by simply moving the sample 14 in a coaxial fashion with respect to the x-ray beam. The sample 14 may be moved to any desired position between the x-ray reflector 35 and the detector 16 to create different combinations of flux strength, angular range, and resolution. The detector 16 may also be moved for certain applications.

Figure 5A:
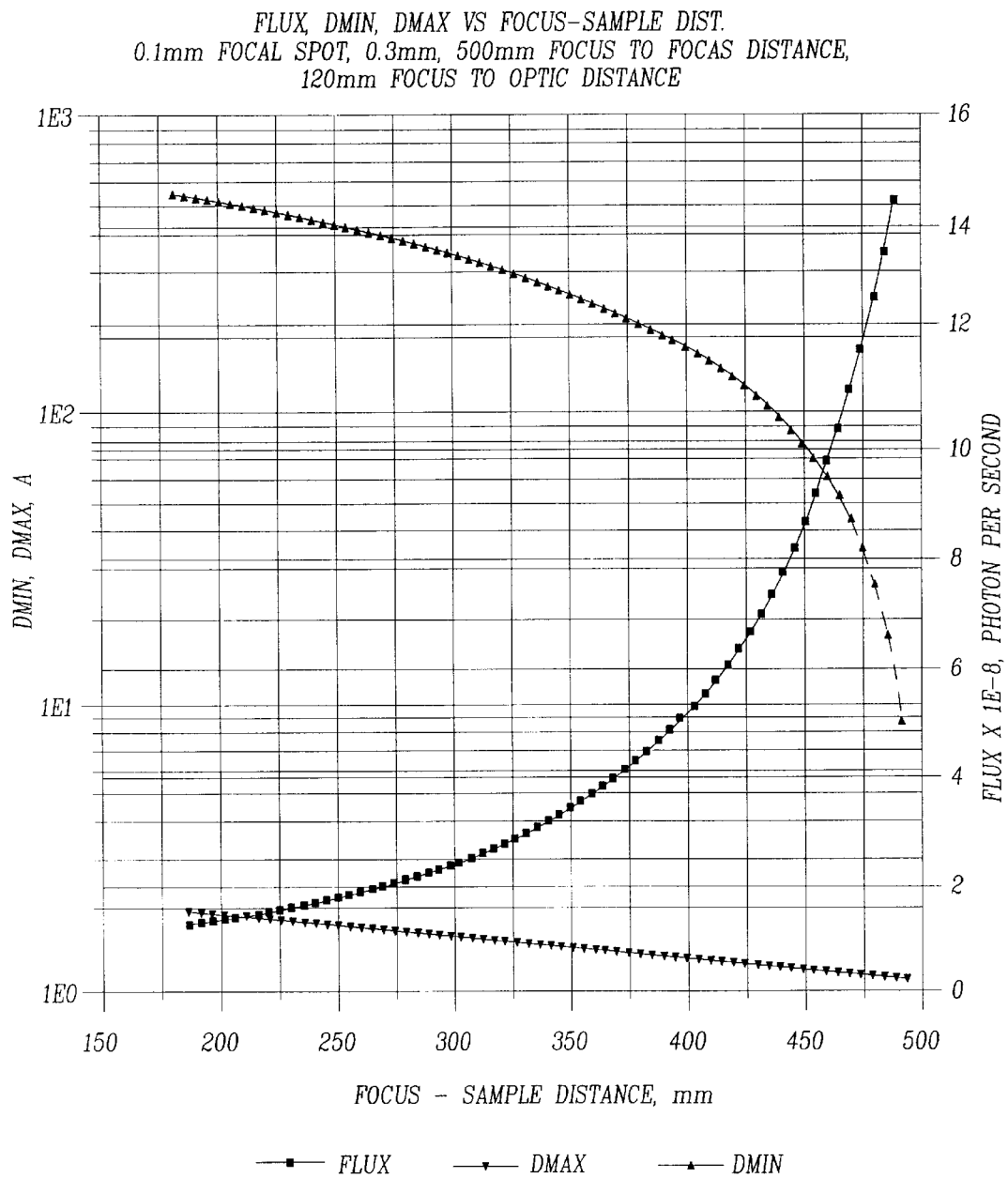
FIGS. 5a and 5b are graphs which illustrate the relationship between the maximum and minimum measurable values of d-spacing within the sample structure for a specified configuration.
Figure 5B:
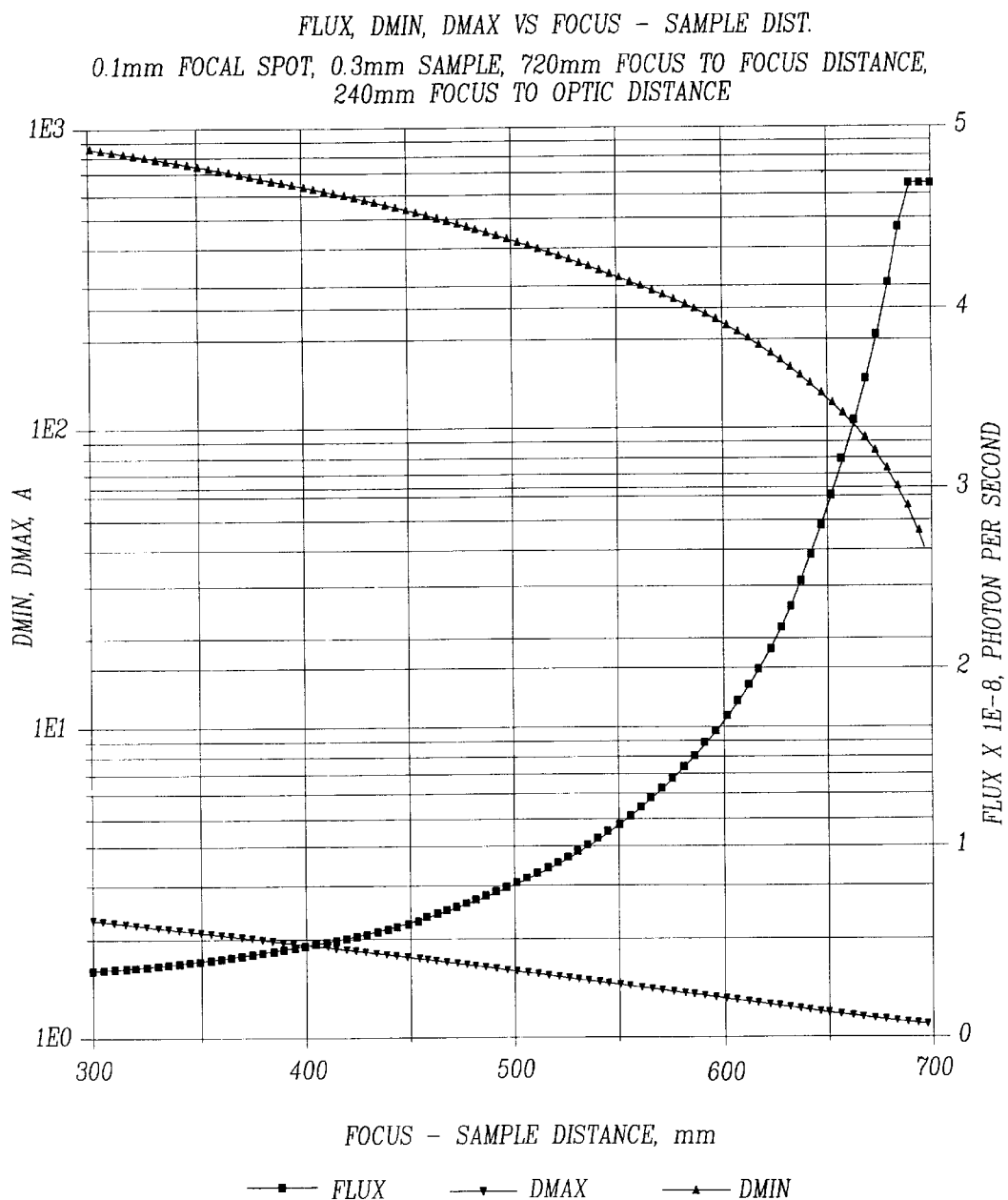

FIG. 5a and 5b are graphs which illustrate the relationship between the maximum and minimum measurable values of d-spacing within the sample structure for a specified configuration. The maximum value $d_{max}$ is the maximum value of d-spacing, which allows a diffracted pattern to be resolved from a direct x-ray beam and is calculated as:

$$d_{max} = \frac{\left(\frac{\lambda}{2}\right)}{\sin\left(\frac{B_m}{L_{sd}}\right)}$$

where $\lambda$ is the wave length of the x-ray beam, $B_m$ is the full width of the pattern, and $L_{sd}$ is the sample-detector distance. This relation implies that two maxima are resolved if the distance between the two spots is equal to twice the full width of the beam spots.

The minimum value $d_{min}$ denotes d-spacing of the sample which causes a diffracted x-ray beam to fall at the limits of the detector area and is calculated as:

$$d_{min} = \frac{\left(\frac{\lambda}{2}\right)}{\sin\left(\arctan\left(\frac{\left(\frac{D_d}{2}\right)}{\left(\frac{L_{sd}}{2}\right)}\right)\right)}$$

where $\lambda$ is the wave length of the x-ray beam, $L_{sd}$ is the sample-detector distance, and $D_d$ is a diameter of the working area of the detector.

Figure 6:
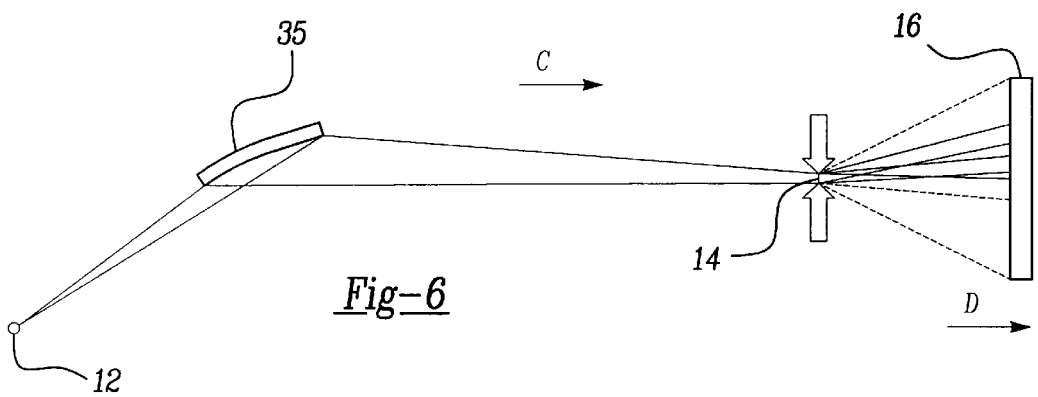
FIG. 6 is a diagrammatic view of a sample placed at the focal point of a reflecting optic.

For extremely small samples, there must be a large flux density upon the sample to generate enough diffraction to produce a registerable diffraction pattern. In FIG. 6 a sample 14 has been moved on to the focal point of x-ray reflector 35 and the detector 16 has been moved from the focal plane. At this point the flux on the sample 14 can be increased to the maximum possible and the diffraction pattern will be at its greatest intensity. The detector 16 may be moved to vary the diffraction pattern.

Figure 7:
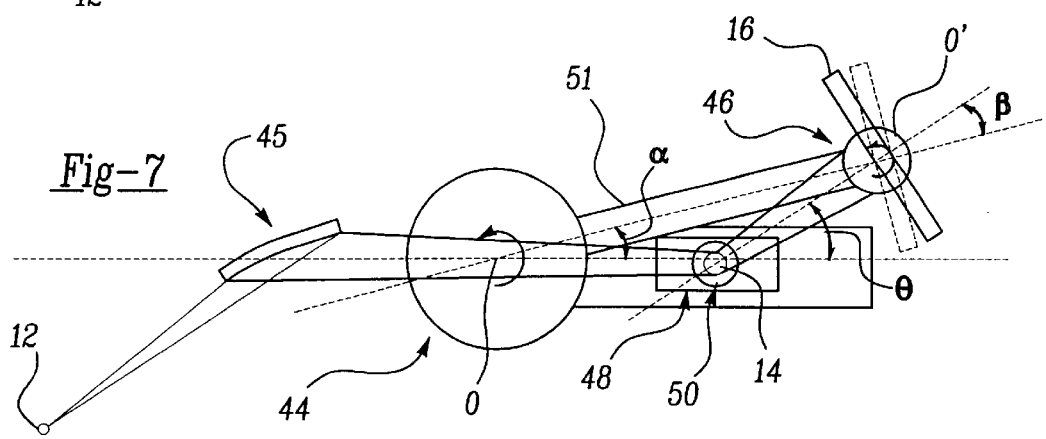
FIG. 7 is a diagrammatic view of a second embodiment of the present invention illustrating its method of operation.

FIG. 7 is a diagrammatic view of a second embodiment of the present invention, illustrating its method of operation. An x-ray source 12 directs x-rays to an elliptical multilayer or graded-d multilayer mirror 45 which acts as a Bragg reflector. The x-rays are incident upon sample 14 which produces a diffraction pattern registered by x-ray detector 16. The sample 14 is positioned by a sample translation stage 48 and rotated by a sample goniometer 50 in at least one direction. The translation stage 48 may be comprised of any method of actuation including motorized or manual screws, slides, pneumatic cylinders and hydraulic cylinders but is not limited to these methods. The x-ray detector 16 is mounted to a swing arm 51 which is coupled to goniostat 44. A goniostat is a goniometer on top of which one can place multiple components. The swing arm 51 allows the detector 16 to be rotated about the axis of the goniostat 44, increasing the angular range measurements of the system. The detector 16 is also rotatable about itself, giving the system another degree of angular freedom. The rotation of the swing arm 51 and the rotation of the detector 16 about itself will provide for the rotation of the detector 16 about the sample 14.

Diffraction at high angle can be measured by either using a large detector or rotating the detector. The rotation is achieved by rotating about O and O'. If θ is the desired angle the two rotations are needed.

$$\alpha = \sin^{-1}\left(\frac{u\sin^{-1}\theta}{L}\right) \quad \theta > 0$$

$$\alpha = -\sin^{-1}\left(\frac{u\sin^{-1}|\theta|}{L}\right) \quad \theta < 0$$

$$\theta = \beta + \alpha$$

The swing arm 51 for the detector mounted on the goniostat 44 makes the α rotation. The sample detector 16 mounted on the detector goniometer 46 makes the β rotation. The α and β rotations together give the θ rotation.

While the use of multilayer or graded-d multilayer Bragg reflective surfaces detailed in this invention is the preferred embodiment, sample translation within an x-ray beam can be utilized by a diffractometer equipped with any x-ray optic or x-ray generation technique. For example, a sample may be moved for a diffractometer having traditional total reflection mirrors or x-ray capillary fibers.

Traditional diffraction analysis is not the only x-ray application that will benefit from the use of sample translation and multilayer or graded-d multilayer Bragg reflective surfaces. The following applications may use the techniques and apparatus of the present invention: protein crystallography using x-ray diffraction techniques to study the atomic structure of protein crystals, nucleic acids, and other biological substances; small molecule diffraction to determine the structure of molecules designed to explore specific chemical phenomena to determine the absolute structure of organic and inorganic molecules; small angle scattering where x-rays are reflected at a very shallow angle from a sample with the resultant giving an impression of the different particle structures found in the sample; microcrystal diffraction which measures the structural composition of very small crystalline samples by focusing the beam through a small sample; and stress/strain analysis from a metal sample. The present invention is not limited to the listed applications as any x-ray analysis technique will benefit from the sample translation of the present invention.

It is to be understood that the invention is not limited to the exact construction illustrated and described above, but that various changes and modifications may be made without departing from the spirit and scope of the invention as defined in the following claims.

I claim:
1. An x-ray diffractometer system comprising:
   a reflector optic which directs x-rays; and
   a sample holding means, wherein a sample is placed into said sample holding means and said directed x-rays, wherein said sample diffracts said directed x-rays, creating a diffraction pattern, and wherein said sample is movable in a coaxial fashion within said directed x-rays by a translation means, whereby the resolution, angular range, and intensity of said diffraction pattern are capable of being adjusted.
2. The x-ray diffractometer system of claim 1, wherein said reflector optic has a multilayer Bragg reflective surface.
3. The x-ray diffractometer system of claim 1, wherein said reflector optic has a graded-d multilayer Bragg reflective surface.
4. The x-ray diffractometer system of claim 3, wherein said graded-d multilayer Bragg reflective surface is depth graded.
5. The x-ray diffractometer system of claim 3, wherein said graded-d multilayer Bragg reflective surface is laterally graded.
6. The x-ray diffractometer system of claim 1, wherein said reflector optic is a total reflection mirror.
7. The x-ray diffractometer system of claim 1, wherein said reflector optic is a capillary fiber system.
8. The x-ray diffractometer system of claim 1, wherein said reflector optic is elliptically shaped.
9. The x-ray diffractometer system of claim 1, wherein said reflector optic is shaped as a partial ellipsoid.
10. The x-ray diffractometer system of claim 1, wherein said reflector optic is cylindrically shaped.
11. The x-ray diffractometer system of claim 1, wherein said reflector optic is spherically shaped.
12. The x-ray diffractometer system of claim 1, further comprising an x-ray detector to detect said diffraction pattern, wherein said x-ray detector is mounted to a goniostat for movement in a circular manner about said goniostat axis.
13. The x-ray diffractometer system of claim 12, wherein said x-ray detector is rotatable about itself.
14. The x-ray diffractometer system of claim 1, further comprising a translation stage coupled to said sample holding means, whereby said translation stage moves said sample throughout said directed x-rays.
15. The x-ray diffractometer system of claim 1, further comprising a goniometer coupled to said sample holding means, wherein said goniometer spins said sample in at least one direction.
16. An x-ray diffractometer system comprising:
    a focusing x-ray optic which focuses x-rays;
    a sample holding means for placing a sample into said focused x-rays, wherein a portion of said focused x-rays travels through said sample, said sample diffracting said focused x-rays, creating a diffraction pattern; and
    a translation stage coupled to said sample for moving said sample coaxially within said focused x-rays, whereby the resolution, angular range, and intensity of said diffraction pattern are capable of being adjusted.
17. The x-ray diffractometer system of claim 16, wherein said focusing optic has a multilayer Bragg reflective surface.
18. The x-ray diffractometer system of claim 16, wherein said focusing optic has a graded-d multilayer Bragg reflective surface.

19. The x-ray diffractometer system of claim 18, wherein said graded-d multilayer Bragg reflective surface is depth graded.

20. The x-ray diffractometer system of claim 18, wherein said graded-d multilayer Bragg reflective surface is laterally graded.

21. The x-ray diffractometer system of claim 16, wherein said focusing x-ray optic is a total reflection mirror.

22. The x-ray diffractometer system of claim 16, wherein said focusing x-ray optic is a capillary fiber system.

23. The x-ray diffractometer system of claim 16, wherein said focusing x-ray optic is elliptically shaped.

24. The x-ray diffractometer system of claim 16, wherein said focusing x-ray optic is shaped as an ellipsoid.

25. The x-ray diffractometer system of claim 16, wherein said focusing x-ray optic is cylindrically shaped.

26. The x-ray diffractometer system of claim 16, wherein said focusing x-ray optic is spherically shaped.

27. The x-ray diffractometer system of claim 16, further comprising an x-ray detector to register said diffraction pattern, wherein said x-ray detector is mounted to a goniostat for movement in a circular manner about said goniostat axis.

28. The x-ray diffractometer system of claim 27, wherein said x-ray detector is rotatable about itself.

29. The x-ray diffractometer system of claim 27, wherein said x-ray detector is movable along said goniostat arm.

30. The x-ray diffractometer system of claim 16, further comprising a translation stage coupled to said sample holding means, whereby said translation stage moves said sample throughout said directed x-rays.

31. The x-ray diffractometer system of claim 16, further comprising a goniometer coupled to said sample holding means, wherein said goniometer spins said sample in at least one direction.

32. A method of generating and registering an x-ray diffraction pattern of a sample comprising:

generating x-rays;

directing said x-rays at a sample;

translating said sample coaxially through said x-rays;

creating a diffraction pattern from said sample; and detecting said diffraction pattern.

* * * * *

UNITED STATES PATENT AND TRADEMARK OFFICE
CERTIFICATE OF CORRECTION

PATENT NO. : 6,069,934
DATED : May 30, 2000
INVENTOR(S) : Boris Verman et al.

It is certified that error appears in the above-identified patent and that said Letters Patent is hereby corrected as shown below:

Column 1,
Line 58, delete "d" and insert therefor -- *d* --

Column 6,
Line 60, delete "coaxially" and insert therefor -- linearly --

Signed and Sealed this

Seventh Day of August, 2001

*Attest:*

NICHOLAS P. GODICI
*Attesting Officer* *Acting Director of the United States Patent and Trademark Office*